US006493601B1

(12) United States Patent
Wells et al.

(10) Patent No.: US 6,493,601 B1
(45) Date of Patent: Dec. 10, 2002

(54) REAL TIME MEASUREMENT SYSTEM FOR A MOVING WEB USING A KALMAN FILTER ALGORITHM

(75) Inventors: Charles H. Wells, Redwood City; Eugene Pertsov, San Jose, both of CA (US)

(73) Assignee: Impact Systems, Inc., Los Gatos, CA (US)

( * ) Notice: Subject to any disclaimer, the term of this patent is extended or adjusted under 35 U.S.C. 154(b) by 0 days.

(21) Appl. No.: 09/336,604

(22) Filed: Jun. 18, 1999

(51) Int. Cl.[7] .................................................. G06F 7/66

(52) U.S. Cl. ....................... 700/128; 700/127; 700/129; 700/122; 700/89; 101/92

(58) Field of Search .............................. 700/31, 37, 45, 700/52, 72, 89, 105–106, 117, 122–123, 127–128, 130, 148, 167, 176, 282

(56) References Cited

U.S. PATENT DOCUMENTS 5,796,609 A * 8/1998 Tao et al. ................... 364/164
5,991,525 A * 11/1999 Shah et al. ............ 395/500.23
6,322,666 B1 * 11/2001 Luontama et al. .......... 162/198
6,368,461 B1 * 4/2002 Ruf et al. ................... 162/258

OTHER PUBLICATIONS

Mohan Malladi et al., "Gauss–Markov model formulation for the estimation of time–varying signals and systems," TENCON '98. 1998 IEEE Region 10 International Conference on Global Connectivity, vol. 1, pp. 166–169, 1998.*

Raman K. Mehra, "Estimation theory," McGraw–Hill Encyclopedia of Science & Technology, McGraw Hill, Inc., 7th Edit., vol. 6, pp. 483–486.

* cited by examiner

*Primary Examiner*—Thomas Black
*Assistant Examiner*—Crystal J Barnes
(74) *Attorney, Agent, or Firm*—Coudert Brothers LLP

(57) ABSTRACT

A Kalman filter algorithm is used for estimation in a feedback control system for a moving web. Matrices of the Kalman filter algorithm are solved with reduced computational complexity. One of the matrices is solved as a diagonal matrix for both state prediction and covariance and another matrix for gain is solved merely as a vector.

6 Claims, 2 Drawing Sheets

REAL TIME MEASUREMENT SYSTEM FOR A MOVING WEB USING A KALMAN FILTER ALGORITHM

The present invention is directed to a real time measurement system for a moving web using a Kalman filter algorithm and, more specifically, to measurements on a web which are based on a mechanical scanning sensors traversing across the moving web.

BACKGROUND OF THE INVENTION

In feedback control processes for moving webs and especially in the paper-making industry, a scanning sensor traverses the web and measures a parameter such as basis weight, moisture, caliper or coating. Also, the same is true in other industries such as metal rolling and the manufacture of fabric, rubber and flooring materials. As will be described in conjunction with the preferred embodiment, when a scanner is scanning across a moving sheet the sampling or measurement intervals (databox values) are not equal due to both the back-and-forth scanning movement and the so-called offsheet turn-around time. But for good feedback control, it is desired to provide continuous estimates of the entire perpendicular profile under the scanner each time one of many so-called databox measurements is made. Thus, it is desired to generate a cross direction profile estimate as if they were generated from a non-scanning device.

What is desired is optimal state estimation of the profile. It is known that a Kalman filter in conjunction with the Gauss-Markov process equations theoretically can do this. But differential matrix equations including exponential matrices must be solved and when these may involve matrices of 240×240 once every 20 milliseconds, computational complexity makes standard use of the Kalman filter impossible. And this is especially true of a scanning process where, for example in a paper-making process where the paper sheet moving several feet per second, means that any effective feedback control must be quickly accomplished.

The Kalman filter algorithm is well-known in estimation theory as fully described in the McGraw-Hill Encyclopedia of Science and Technology, Vol. VI, 7th Edition, pp 483–486.

OBJECT AND SUMMARY OF INVENTION

It is a general object of the present invention to provide an improved real time measurement process for a moving web.

In accordance with the above object, there is provided a real time measurement process for a moving web where a scanning sensor traverses the web and a measured parameter is fed back via a computer on-line to control an actuator which can change the parameter and where measurement or sampling intervals are not equal, and where the scanning sensor has a plurality of databox measurement positions as it scans across the web, the process comprising the following steps of using the Kalman filter algorithm to predict and update values of said parameter to provide continuous values for said feedback control including using the Gauss-Markov equation $$y(t)=H(t)\times(t)+u$$

where y(t) is the observed parameter value, H is a matrix which is dependent on databox position of the scanner and which changes with each different databox measurement and u is a scalar representing the noise associated with each measurement, and where the H matrix is solved by the computer not as a matrix but as a vector to significantly reduce computational complexity.

DETAILED DESCRIPTION OF PREFERRED EMBODIMENT

Figure 1:
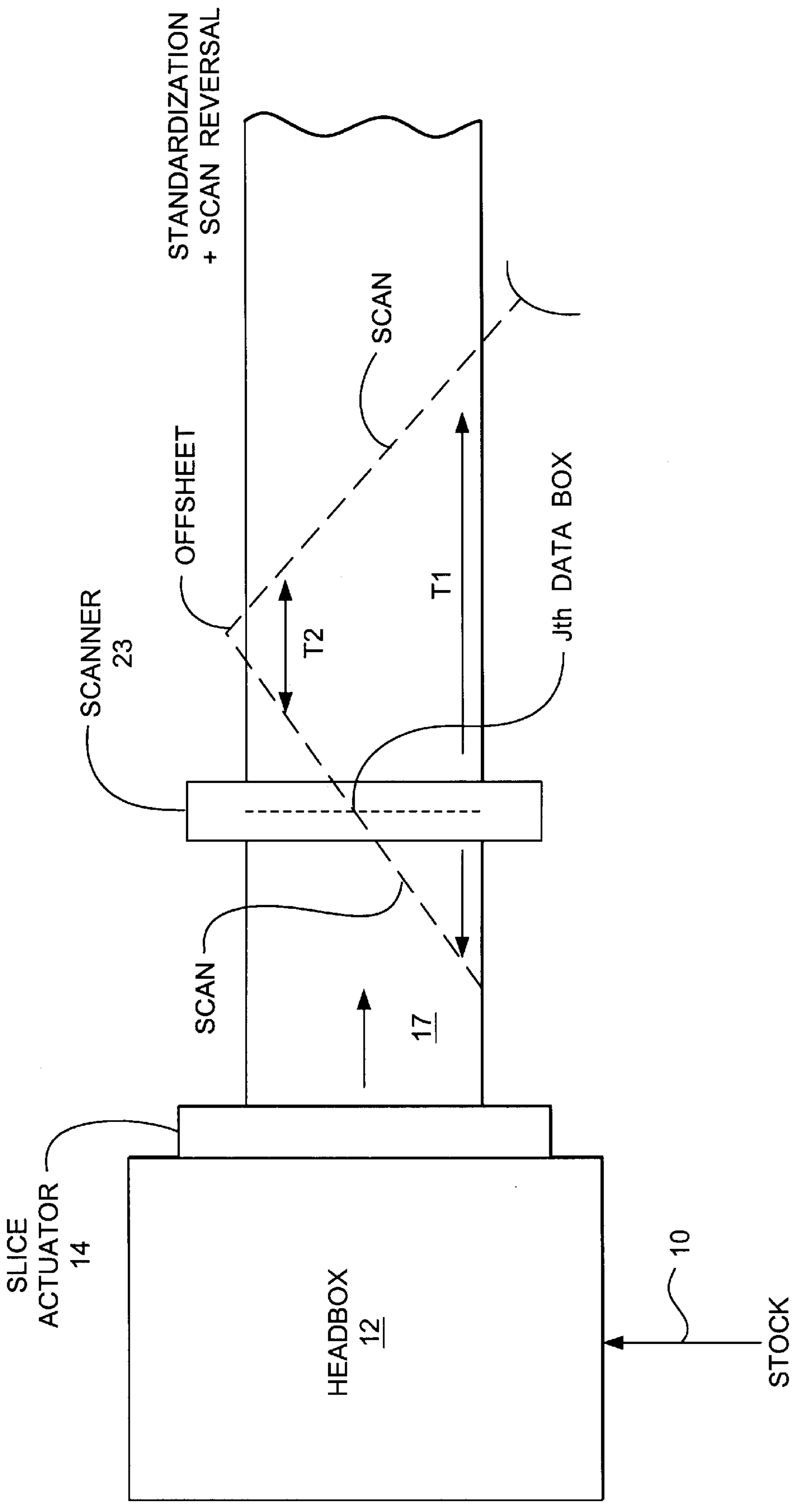
FIG. 1 is a simplified top view of a paper-making machine illustrating the present invention.

A FIG. 1 illustrates conceptually a measurement process for the moving web or paper sheet of a paper-making process. Here, a headbox 12 has pulp slurry fed through a stock input valve and pipeline 10 (which may be varied in accordance with a control unit to be discussed later). The pulp slurry is outputted in the form of a wet web 17 through a slice actuator 14. A scanner 23 located over the web 17 scans across the width of the paper approximately every 20 seconds to provide a measurement of output parameters or variables such as basis weight (B.W.), moisture (MOI) and also other parameters such as caliper and coating. The actual effective scan, however, indicated by the diagonal scan lines and the back-and-forth movement includes an offsheet position for both scan reversal of the scanning head and also for standardization of the measurement system. The scanner produces a measurement at a selected number of databoxes indicated as j databoxes ten of which may correspond to a predetermined slice width. The jth databox is indicated as being measured at the present time in FIG. 1. By inspection, it is obvious that the times, for example, T1 and T2 between databoxes are not uniform. Also, the back-and-forth scanning along with standardization and scan reversal time produces sampling intervals which are not equal.

It is desirable, however, for the purpose of feedback control to estimate the entire perpendicular profile under the scanner each time a new databox measurement is made. The change of parameter value between adjacent databoxes is known as the covariance function which is designated $P_i$ which is the estimated covariance of the state vector at the time i. The state vector, $X_i$, is, of course, the estimate of the cross-direction profile of the moving sheet at the scanner time i. Measurements in the machine direction, that is, the direction of the moving web, can also be estimated and predicted. In general, and this is related to the Kalman filter algorithm used in estimating, there are five steps to the estimation process which will be described in detail below:

(1) prediction of a state vector;

(2) prediction of a covariance matrix;

(3) calculation of the Kalman gain;

(4) update of state prediction; and (5) update of covariance matrix.

The state vector is an (n×1) vector containing the best estimate of the (n) databox values in the perpendicular profile in line with the scanner.

Figure 2:
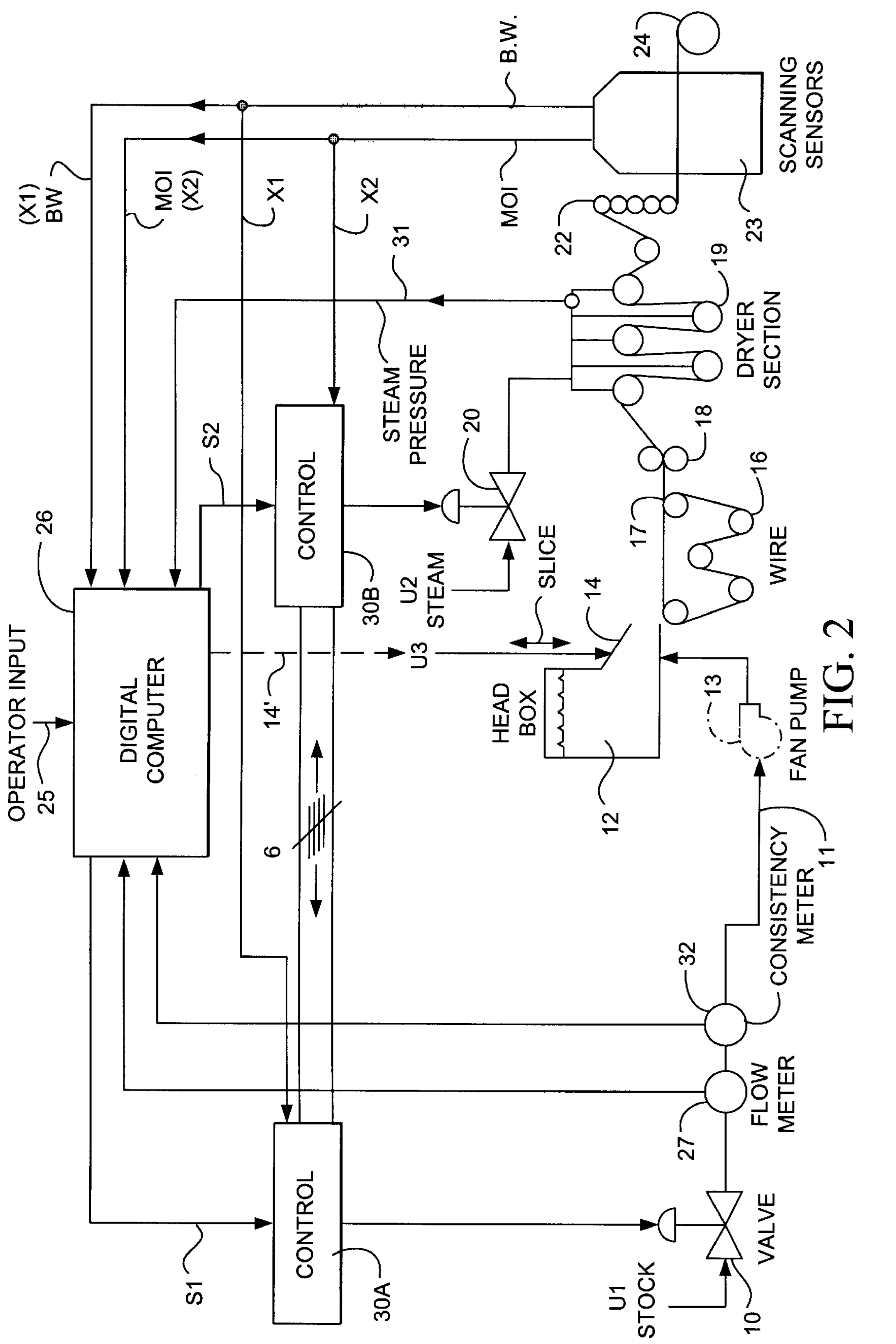
FIG. 2 is a block diagram of a detailed paper-making machine including auxiliary equipment such as control computer and scanning units.

The actual physical configuration of a typical paper-making machine including associated control hardware and software is illustrated in FIG. 2. Here, raw paper stock is supplied to the machine via a stock valve 10 and a stock line 11 to a head box 12 by a fan pump 13. The pump and water mixture jets from head box 12 through a slice 14 on top of and parallel to wire 16. This forms a wet web 17, which on leaving wire 16 passes through rollers 18, which remove much of the water from the web and essentially converts it to a sheet of wet paper. Thereafter, the paper sheet passes through a dryer section 19 consisting of several rollers to which steam is supplied by steam control valve 20. Steam heats the rollers and, consequently, evaporates much of the water in the paper sheet so that the paper emerging from the dryer section 19 has the desired moisture content MOI. Thereafter, the paper passes through a calendar stack 22 through scanning sensors 23 and is wound on the reel 24.

Scanning sensors 23 scan across the width of the paper approximately every 20 seconds and provide a measurement of the output variables of B.W. and moisture MOI. The two output variables from the scanning sensors 23 are also designated X1 and X2. The scanned moisture and basis weight values are coupled to the digital computer 26 for processing along with an operator input 25. Digital computer 26 also provides via the line 14' a control output U3 which provides for slice adjustment. Typically, in the cross direction of the paper, 240 measurements are made. Controller portion 30A has as inputs a setpoint S1 from the digital computer 26 and X1 and as an output, the control value U1, which drives the stock valve 10 to provide a dry stock (fiber) flow rate of U1. Similarly, controller portion 30B receives the setpoint S2 (actually, the steam pressure) from digital computer 26 along with X2 and by its output U2 drives the steam valve 20 to provide a U2 steam input. Controller portions 30A and 30B are connected by a cable 6.

Digital computer 26 has as other feedbacks the steam pressure line 31 from dryer section 19 and also flow meter 27 and a consistency meter 32, which determine the pounds per minute of dry stock flow.

To utilize the Kalman filter algorithm in an estimation system, a process model is required which is based on the physical process that takes place in the web-forming machine. In the specific case of a paper machine, this means that the pulp slurry in the head box (that is, the liquid mass) in effect is a mass balance around a small volume. If "x" is denoted as an amount of liquid mass (i.e., Basis Weight) of one particular databox, the rate of mass input to the databox for a small interval $\Delta t$ is b•u $\Delta t$, where 'u' is control input (U3) (slice lip opening), and "b" is coefficient. The mass leaving the volume consists of two parts: the amount is leaving in the machine direction with speed "v":x/L•v•$\Delta t$, where L is the size of one databox in machine direction, and the amount that exits in both CD (cross directions) into adjacent databoxes (the rate of mass flux) is proportional to the difference between masses of these databoxes times some coefficient "a," i.e., the diffusion coefficient of equation (1). See the equations page at the end of this specification.

Equation 1 is a mass balance equation which is essentially made equal to zero. The terms $x_i$ and $x_{i+1}$ are the values of adjacent databoxes. The foregoing assumption follows Fick's law of mass diffusion which is from a broad definitional standpoint that the rate of diffusion of a matter moving across a plane is proportional to the negative of the perpendicular rate of change of concentration. Thus, the foregoing assumption following Fick's law, the total mass balance for the databox "I" will be equation (2).

Dividing both sides by $\Delta t$, and taking the limit as $\Delta t$ goes to zero, we have equation (3).

Denoting $T=1/(v+2a)$ and $\alpha=a\ (v+2a)=\alpha \bullet T$ and taking into account that measurements are delayed by time $\theta_A$, and adding random disturbance $\eta$, yields equation (4).

In equation (4), T is a time constant, x is a state vector of 'n' dimension, A is a matrix of (n×n) dimension as illustrated which represents the intrinsic dynamics of the system, u is a vector of m dimensions which may be, for example, the number of slices or zones across the paper web. Typically, the "state" dimension exceeds 200 databoxes in current paper-making applications and the number of actuator zones is less than 100. The foregoing results in a computationally intractable problem unless the Kalman filter algorithm is solved by unique techniques which will be described below.

In the present simplified consideration, the time constant T represents the time of measuring of one databox (≈0.1 sec.). In more realistic case, T can represent the mixing time constant in the databox. Typically, this constant is in the order of several to 10 seconds in medium to large mills. This is basically the time from the slice lip to the "dry-line." The B matrix represents the "mapping" matrix from actuators to the scanner. This is a non-square matrix, since there are normally many more databoxes than actuator zones. The time delay between the actuator and the scanner is $\theta_A$ seconds. A good estimate of this delay may be found by dividing the sheet run distance by the machine speed. This delay is typically 60 to 180 seconds. The disturbance or noise term is $\eta$.

Without disturbances, equation (4) can be rewritten as equation (5).

If U is equal to a constant over the time interval t, the solution of equation (5) is given by equation (6) which can be used for a state prediction:

The foregoing equation (6) is a rewritten form of one of the two Gauss-Markov process equations. The other equation for the measurement function is of the form of equation (7).

Although only one measurement is made of one component of the state vector x at a time, all n states are estimated. Thus, the H-matrix is a function of a databox position: i.e., it changes with each different databox measurement. Thus, if only one databox j is measured, all other members are equal to zero. The essential part of the approach of the present invention is the formulating of the measurement of one databox measurement at a time as a highly structured time varying matrix. The U value is a scalar representing noise.

State prediction is based on equation (6).

For the interval between two databox times, see equation (7'); when conditionally integrated it yields the Equation 8 which assumes U is constant over the interval of Equation (7').

In order to perform these calculations, the matrix exp(-($\tau$/T)A) is calculated for each time interval since the time interval during the scanner head turn-around is much longer than one databox interval; otherwise, this matrix could be computed once at the beginning of the execution.

The foregoing can be calculated using the formula of equation (9)

Where D is a constant diagonal matrix derived from A, and W is a constant matrix; see equation (10).

Such matrix always exists because A is symmetric. Additionally, since the interval from the last databox of a previous scan is not known until the first databox of the next scan, this matrix must be calculated for each new measurement.

Thus, the exponential matrix for each interval must be calculated or computed since the time intervals are unequal. Normally, this would be a constant matrix if the time intervals between measurements were constant. That is, the exponential matrix would be calculated once at the beginning of each scan. However, for unequal time intervals the calculations of the matrix must occur each databox or measurement time normally taking on the order of $N^2$ computations. In the case of a paper-making machine, or other web process this is a dimensional task of too much complexity for other than a super computer.

Thus, in order to reduce computational complexity of the A matrix, numeric experiments show that for a wide span of time the exponent matrix, see Equation 8, can be considered as a narrow-banded matrix that has essential values only near the main or principal diagonal. In other words, it can be solved as a diagonal matrix.

Such a matrix is defined (see McGraw-Hill Encyclopedia of Scientific and Technical Terms, 5th Edition) as a matrix where the non-zero entries all lie on the principal diagonal. While this is not totally true of the present exponential matrix, values other than the main diagonal are only second order. Thus, in the solving of this as a diagonal matrix, the time of calculation does not depend on the dimension of the task; that is the complexity of the calculations is a function of not $n^2$ but only n.

Another prediction used in the standard Kalman filter algorithm is illustrated in equation (11) which is a covariance prediction:

Because the A matrix is symmetric and also the exponential value is symmetric, no transposition need be performed. The Q matrix can easily be computed without undue complexity by well-known techniques. This is illustrated in equation (12).

Because of unequal sampling, intervals must be computed at each measurement time.

The Kalman gain matrix is defined as equation (13).

Each time a databox j is measured, the matrix H becomes "one" with all the other elements equaling zero. R is a diagonal matrix with all equal elements so that equation (14) has only one non-zero element; that is equation (15).

Therefore, matrix K has only one non-zero column J as shown in equation (16).

Hence, K can be maintained not as a matrix but as a vector which is simply solved and where computational complexity is reduced.

Continuing with the typical Kalman solution for state update, equation (17) is utilized which can be transformed into equation (18) and where the y vector is defined in equation (19).

Again, complexity is significantly reduced.

Finally, for updating the covariance matrix using previous results, equation (20) and the accompanying matrix result which again is a diagonal-type matrix where computational complexity is significantly reduced.

Finally, as a default only the H matrix need be computed as in the equations where it is relevant and the A function can be set to a constant or the last resulting value. This assumes that no change in the physical process model takes place.

Thus, an improved Kalman filter-type estimation system has been provided with reduced computational complexity.

EQUATIONS $\alpha\cdot((x_i-x_{i-1})+(x_i$ $-x_{i+1}))\cdot\Delta t$ (1)

$\Delta x_i=-{}^{v}\!/_{L}\cdot x_i\cdot\Delta t-\alpha\cdot(($ $x_i-x_{i-1})+(x_i-x_{i+1}))\cdot\Delta$ $t+b\cdot u\cdot\Delta t$ (2)

+i ẋ+l $_i=-v\cdot x_i-$ $\alpha\cdot((x_i-x_{i-1}))+(x_i-x_{i+1}))+b\cdot u$ (3)

+i ẋ+l $(t)=-{}^{1}\!/_{T}Ax(t)+Bu(t-\theta_A)+\eta$ where $$A=\begin{bmatrix} 1 & -\alpha & & & \\ -\alpha & 1 & -\alpha & & \\ & -\alpha & \dots & -\alpha & \\ & & -\alpha & 1 & -\alpha \\ & & & -\alpha & 1 \end{bmatrix}, \tag{4}$$

$TA^{-1}$+i ẋ+l $(t)+x(t)=U(t)$, where $$U=T\cdot A^{-1}\cdot b\cdot u. \tag{5}$$

$$x(t_{i+1}\mid t_i)=\exp\left(-\frac{\tau_i}{T}A\right)x(t_i)+\left(I-\exp\left(-\frac{\tau_i}{T}A\right)\right)\cdot U \quad (2.1) \tag{6}$$

$$y(t_i)=H(t_i)\cdot x(t_i)+\mu \tag{7}$$

$$\tau_i=t_{i+1}-t_i$$

$$x(t)=\exp\left(\frac{\tau_i}{T}A\right)x(0)+\left(I-\exp\left(-\frac{t}{T}A\right)\right)\cdot U, \tag{8}$$

$$\exp\left(-\frac{\tau_i}{T}A\right)=W^{-1}\cdot\exp\left(-\frac{\tau_i}{T}D\right)\cdot W \tag{9}$$

$$D=W\cdot A\cdot W^{-1} \tag{10}$$

$$P'(t_{t+1})=\exp\left(-\frac{\tau_i}{T}A\right)P(t_i)\exp\left(-\frac{\tau_i}{T}A\right)^T+Q(\tau_i) \tag{11}$$

$$Q(\tau)=qI\Delta t\left(\frac{T}{2\Delta t}A^{-1}\right)\left[I-\exp\left(-\frac{2\tau}{T}A\right)\right]=\frac{qT}{2}A^{-1}\left[I-\exp\left(-\frac{2\tau}{T}A\right)\right] \tag{12}$$

$$K(t_i)=P'(t_{i+1})H^T[HP'(ti+1)H^T+R]^{-1} \tag{13}$$

$$H^T[HP'(t_{i+1})H^T+R]^{-1} \tag{14}$$

$$\frac{1}{r+p'_{j,j}} \tag{15}$$

$$K^j=\frac{1}{r+p'_{j,j}}\begin{bmatrix} p'_{1,j} \\ p'_{2,j} \\ \cdot \\ \cdot \\ p'_{n,j} \end{bmatrix} \tag{16}$$

$$x(t_{i+1})=x(t_{i+1}|t_i)+K[z(t_{i+1})-Hx(t_{i+1}|t_i)] \tag{17}$$

$$x(t_{i+1})=x(t_{i+1}|t_i)+y \tag{18}$$

$$y=K\cdot(z_j-x_j(t_{i+1}|t_i)) \tag{19}$$

$$P(t_{i+1})=(I-K(t_i)H)P'(t_{i+1})$$

$$(I - K(t_i)H) = \begin{bmatrix} 1 & . & -k_1 & . & 0 \\ 0 & 1 & . & . & 0 \\ 0 & . & 1-k_j & . & 0. \\ 0 & . & . & 1 & 0 \\ 0 & . & -k_n & . & 1 \end{bmatrix} \quad (20)$$

Therefore $$p_{l,m} = p'_{l,m} - k_l p'_{j,m}$$

What is claimed is:

1. In a real time measurement process for a moving web where a scanning sensor traverses the web and a measured parameter is fed back via a computer on-line to provide feedback control an actuator which can change the parameter and where measurement or sampling intervals are not equal, and where said scanning sensor has a plurality of databox measurement positions as it scans across the web, the process comprising the following steps:

using the Kalman filter algorithm to predict and update values of said parameter to provide continuous values for said feedback control including using the Gauss-Markov equation $$y(t) = H(t) \times (t) + u$$

where y(t) is the observed parameter value, H is a matrix which is dependent on databox position of said scanner and which changes with each different databox measurement and u is a scalar representing the noise associated with each measurement, and where the H matrix is solved by said computer not as a matrix but as a vector to significantly reduce computational and where said H matrix has only one nonzero column which constitutes said vector.

2. In a real time measurement process as in claim 1, where said scanner goes offsheet every scan to accommodate turn-around and where said parameter varies in accordance with the Gauss-Markov process state equation $$\dot{X}(t) = A \times (t) + Bu + \eta$$

where X is a state vector, A is a matrix representing the intrinsic dynamics of the system, B is a matrix representing the effect of a controlled change to said actuator and $\eta$ is noise, including the step of solving said state equation.

3. In a real time measurement system as in claim 2, including the step of predicting covariance, which is the cross-correlation between adjacent databoxes, of said parameter where an exponential of said A matrix is solved as a diagonal matrix to reduce computational complexity whereby said feedback control is enabled on an online basis.

4. In a real time measurement process as in claim 2, where said A matrix is related to fluid flow in the headbox of a paper making process and where the flow of fluid is described by Fick's law of mass diffusion to provide said diagonal matrix.

5. In a real time measurement process as in claim 1, where said Kalman filter has a Kalman gain which is computed from H as a vector.

6. In a real time measurement process as in claim 1, where estimating a future value of said measured parameter includes the steps of:

(1) prediction of a state vector;

(2) prediction of a covariance matrix;

(3) calculation of the Kalman gain;

(4) update of said state prediction; and (5) update of said covariance matrix.

* * * * *